United States Patent [19]

Strohl, Jr. et al.

[11] Patent Number: 4,905,698
[45] Date of Patent: Mar. 6, 1990

[54] METHOD AND APPARATUS FOR CATHETER LOCATION DETERMINATION

[75] Inventors: Clair L. Strohl, Jr., Norfolk; Michael C. Ferragamo, N. Dighton; Donald A. Kay; Alan R. Shapiro, both of Sharon; Gary R. Whipple, S. Attleboro, all of Mass.

[73] Assignee: Pharmacia Deltec Inc., St. Paul, Minn.

[21] Appl. No.: 243,689

[22] Filed: Sep. 13, 1988

[51] Int. Cl.$^4$ ................................................ A61B 6/12
[52] U.S. Cl. .............................. 128/653 R; 128/737; 600/13; 324/219; 324/239
[58] Field of Search .................. 128/737, 653; 600/11, 600/13, 14, 15; 324/219, 234, 239, 220, 233

[56] References Cited

U.S. PATENT DOCUMENTS

| | | |
|---|---|---|
| 3,622,784 | 11/1971 | Del Guercio . |
| 3,659,588 | 5/1972 | Kahn et al. . |
| 4,416,289 | 11/1983 | Bresler . |
| 4,431,005 | 2/1984 | McCormick . |
| 4,432,369 | 2/1984 | Halvorsen . |
| 4,445,501 | 5/1984 | Bresler . |
| 4,572,198 | 2/1986 | Codrington . |

Primary Examiner—Kyle L. Howell
Assistant Examiner—John C. Hanley
Attorney, Agent, or Firm—Peterson, Wicks, Nemer & Kamrath

[57] ABSTRACT

A method and apparatus (10) for determining accurately the location of the tip (14) of a catheter (16) inside biological tissue is disclosed including a locator (34) having a coil (38) wound axially on a core (36) and a detector (12) in the form of a coil (28) wound on a core (24) removably positionable within catheter (16) adjacent the tip (14). A controller (20) generates AC current to coil (38) to produce an electromagnetic field and compares it with the output voltage developed in coil (28) when the locator (34) comes within close physical proximity to detecetor (12). Locator (34) includes an amber LED indicator (42) which is energized when the locator (34) is behind the detector (12) and the monitored output voltage is in phase with the generated alternating current and includes a red LED indicator (44) which is energized when the locator (34) is beyond the detector (12) and the monitored output voltage is 180° out of phase with the generated alternating current. The controller (20) includes a beeper (48) which provides an audible indicator when energization changes between the indicators (42, 44).

16 Claims, 3 Drawing Sheets

METHOD AND APPARATUS FOR CATHETER LOCATION DETERMINATION

BACKGROUND

The present invention relates generally to a method and apparatus for determining accurately the intravascular location of a catheter inside biological tissue, particularly within veins or arteries, and specifically within the vena cava.

The treatment of certain diseases of the human body often requires the short-term or long-term infusion of drugs, blood products, nutritional or other fluids into the patient's venous or arterial system. When it is necessary to administer these parenteral liquids, it is common practice to make a venipuncture with a cannula and then thread a sterile plastic catheter into the vein. Alternate techniques for vascular access include surgical cut-down or Seldinger entry with a dilator/sheath over a guidewire. For patenteral nutrition, cancer chemotherapy, and frequent antibiotic therapy, the outlet (or tip) of the catheter is positioned in areas of high volume blood flow to avoid damage to the lining (intima) along the blood pathway. The end-point for the intravenous catheter tip is often the superior vena cava. The catheter placement procedure is referred to as central venous catheterization (CVC), and growing experience has increased recognition of the need for accurate positioning of the catheter tip.

In current practice, the conventional method for confirming the correct placement of a therapeutic intravenous catheter within the superior or inferior vena cava is visualization with fluoroscopy or x-ray film. However, additional exposure of the patient and clinical staff to irradiation is a disadvantage, and unnecessary if an alternate method for locating were made available.

Thus, a need exists for providing realtime information for accurately determining the location of a catheter within a patient's body according to external anatomical landmarks which eliminates the cost, time, and hazards of radiation exposure and which does not require expensive, high technology equipment or personnel.

SUMMARY

The present invention solves this need and other problems in determining the location of catheters inside the patient's body by producing an output voltage by a detector which reacts to an alternating current magnetic field. Either the detector or the magnetic field source is removably positionable within the catheter for entry with the catheter, with the detector being secured to the guidewire of the catheter in the most preferred form. By comparing the alternating current provided to create the magnetic field with the output voltage of the detector, indication may be given when the output voltage is in phase with the alternating current, when no output voltage is detected, and when the output voltage is 180° out of phase with the alternating current to thus indicate the relative positions of the magnetic field and the detector with respect to one another.

It is thus an object of the present invention to provide a novel method for determining accurately the intravascular location of a catheter inside biological tissue.

It is thus an object of the present invention to provide a novel apparatus for determining accurately the intravascular location of a catheter inside biological tissue.

It is further an object of the present invention to provide such a novel catheter location determining method and apparatus which do not require exposure to X-rays.

It is further an object of the present invention to provide such a novel catheter location determining method and apparatus operable by clinical staff without requiring extensive training.

It is further an object of the present invention to provide such a novel catheter location determining method and apparatus which are simple to operate.

It is further an object of the present invention to provide such a novel catheter location determining method and apparatus which are inexpensive.

It is further an object of the present invention to provide such a novel catheter location determining method and apparatus which provide realtime information of the catheter location according to external anatomical landmarks.

These and further objects and advantages of the present invention will become clearer in light of the following detailed description of an illustrative embodiment of this invention described in connection with the drawings.

DESCRIPTION OF THE DRAWINGS

The illustrative embodiment may best be described by reference to the accompanying drawings where.

Figures 1, 2:
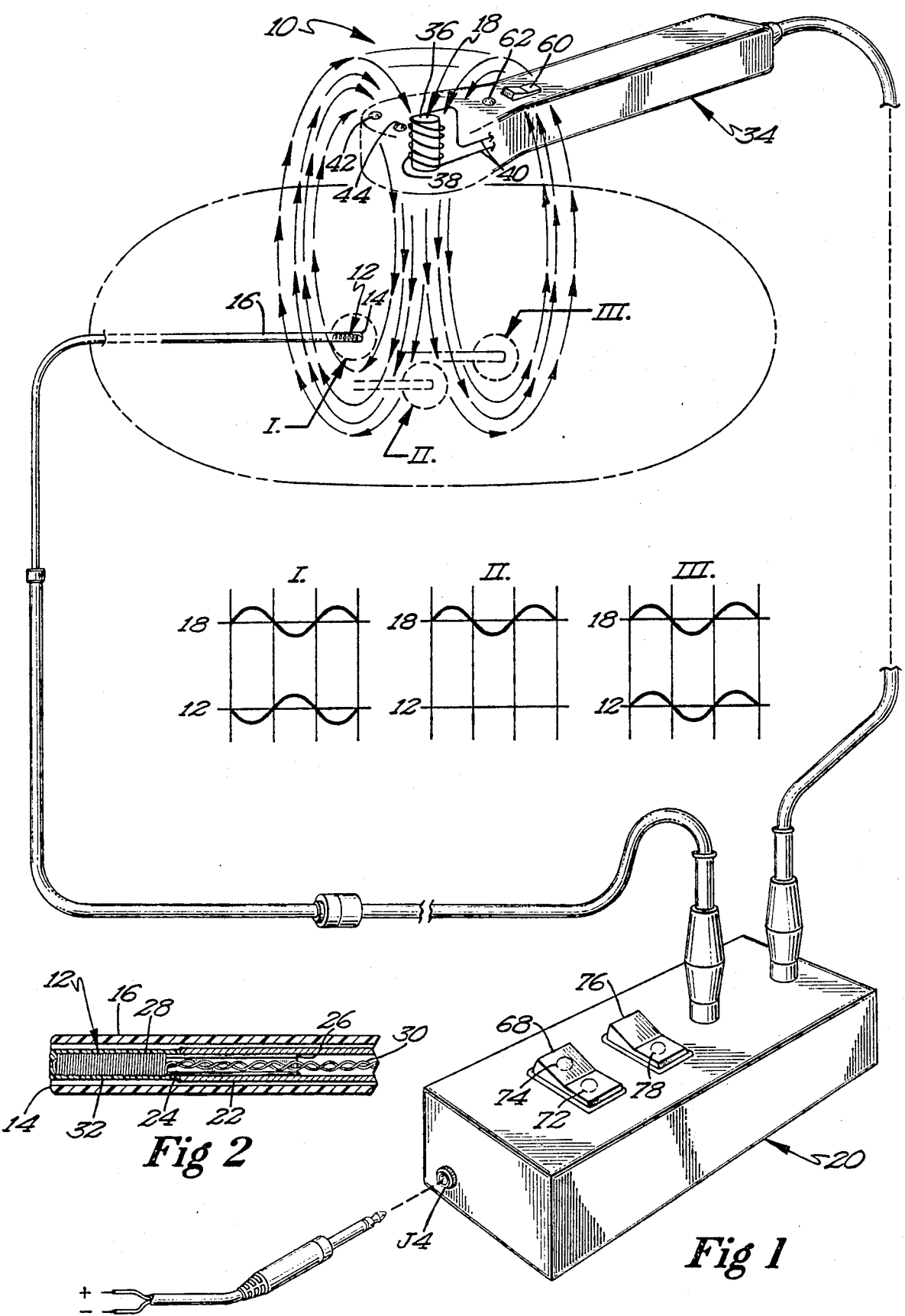
FIG. 1 shows a diagramatic view of a method and apparatus for determining the location of a catheter inside biological tissue according to the teachings of the present invention, with the magnetic field diagramatically shown illustrating an amplitude and polarity existing only an instant in time.
FIG. 2 shows a cross sectional view of a catheter including a detector secured to a guidewire of the apparatus of FIG. 1.

All figures are drawn for ease of explanation of the basic teachings of the present invention only; the extensions of the Figures with respect to number, position, relationship, and dimensions of the parts to form the preferred embodiment will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

Where used in the various figures of the drawings, the same numerals designate the same or similar parts. Furthermore, when the terms "end", "first", "second", "distal", "proximal", and similar terms are used herein, it should be understood that these terms have reference only to the structure shown in the drawings as it would appear to a person viewing the drawings and are utilized only to facilitate describing the invention.

DESCRIPTION

An apparatus for determining the location of the tip of percutaneous catheters or catheters that are part of an implantable access system within veins or arteries of a patient according to the preferred teachings of the present invention is shown in the drawings and generally indicated 10. Generally, apparatus 10 includes an alternating current (AC) electromagnetic energy field pick-up detector 12 which in the preferred form is aligned with the tip 14 of an intravenous catheter 16, an AC electro-magnetic energy source 18, and an electronic controller 20.

Source 18 develops and transmits an AC magnetic field in the preferred form at a coil current in the range of 120 to 200 mA RMS providing in the range of one-quarter to one-half watt at a frequency presently suggested by practical design considerations to be in the range of 50 to 350 kilohertz and in the preferred range of 100 to 200 kilohertz. Source 18 is positionable on the skin at an external anatomical landmark consistent with the desired end-point location of catheter tip 14 with the flux lines of the magnetic field essentially perpendicular to the plane of the skin and projecting into the patient's body. Detector 12 reacts to the AC magnetic field transmitted by source 18 in the preferred form by developing a small voltage when in physical proximity to source 18. Specifically, when the flux lines of the magnetic field transmitted by source 18 are exactly perpendicular to the axis of detector 12, there is zero net flux detected, and therefore no output voltage is developed by detector 12. Furthermore, when detector 12 moves across the line of flux perpendicularity, a phase change occurs in the output voltage developed by detector 12. Thus, by interpreting the phase and level of the voltage developed by detector 12, the orientation or location of the detector 12 with respect to source 18 can be established. Specifically, in the preferred form, electronic controller 20 generates the AC current to produce the electromagnetic field developed by source 18, monitors, processes and amplifies the voltage developed and the phase change of the voltage developed in detector 12, and compares the generated and sensed signals to provide suitable indicators, such as visual and audible signals, of the relative positions of detector 12 and source 18.

In the most preferred form, detector 12 is located in the tip of a hollow cable jacket or guidewire 22 and includes a generally cylindrical core 24 formed of magnetically permeable material and in the most preferred form is solid. Core 24 extends into the free end of guidewire 22 and is suitably secured thereto such as by adhesive 26 located between the inside surface of guidewire 22 and the outer surface of core 24. Core 24 extends beyond the free end of guidewire 22 and includes a coil 28 of fine wire having a diameter in the range of 0.002 inches (0.051 mm) wound thereon coaxially with guidewire 22. In the most preferred form, coil 28 includes in the range of 30 to 60 turns having a diameter of 0.026 inches (0.66 mm). Coil 28 contains leads 30 which extend through the hollow interior of guidewire 22 to controller 20. A coating 32 may be provided covering coil 28 on core 24. Catheter 16 and guidewire 22 may include standard positioning connectors utilized in standard catheter placement techniques.

In the most preferred form, source 18 is located in a locator 34 having a generally elongated shape for grasping by the hand of the operator in a racket fashion. Source 18 includes a generally cylindrical core 36 formed of magnetically permeable material and in the most preferred form is solid. Core 36 in the preferred form is generally perpendicular to the grip axis of locator 34 and includes a coil 38 of fine wire having a diameter in the range of 0.030 inch (0.762 mm) wound axially thereon. In the most preferred form, coil 38 includes in the range of 80 to 100 turns having a diameter of 0.71 inches (1.80 cm). Coil 38 contains leads 40 through the hollow interior of locator 34 to controller 20.

In the most preferred form, locator 34 includes members for providing visual and audible indicators. Specifically, amber and red LED indicators 42 and 44, respectively, are provided on locator 34 and a sound transducer such as a beeper 48 may be provided in controller 20. In the most preferred form, amber indicator 42 indicates that source 18 is proximal to tip 14 of catheter 16 and red indicator 44 indicates that source 18 is distal to tip 14 of catheter 16. Suitable leads 50 are provided to indicators 42 and 44 to controller 20. Additionally, an on-off switch 60 including a visual display 62 such as a green LED indicator in series is electrically connected to controller 20 by suitable leads 64.

Figure 3A:
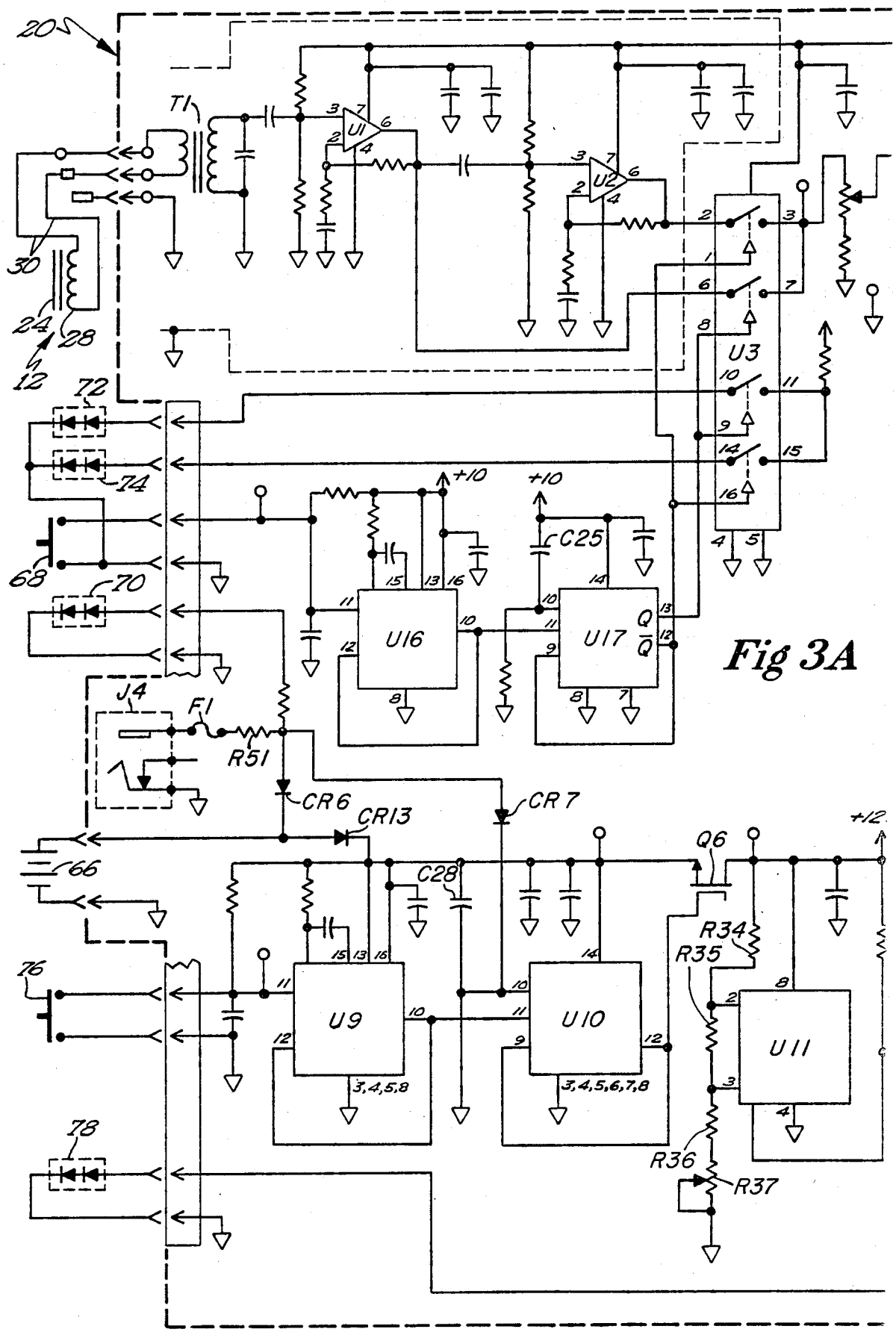
FIGS. 3A and 3B, when placed together, constitute an electrical schematic for the apparatus of FIG. 1.
Figure 3B:
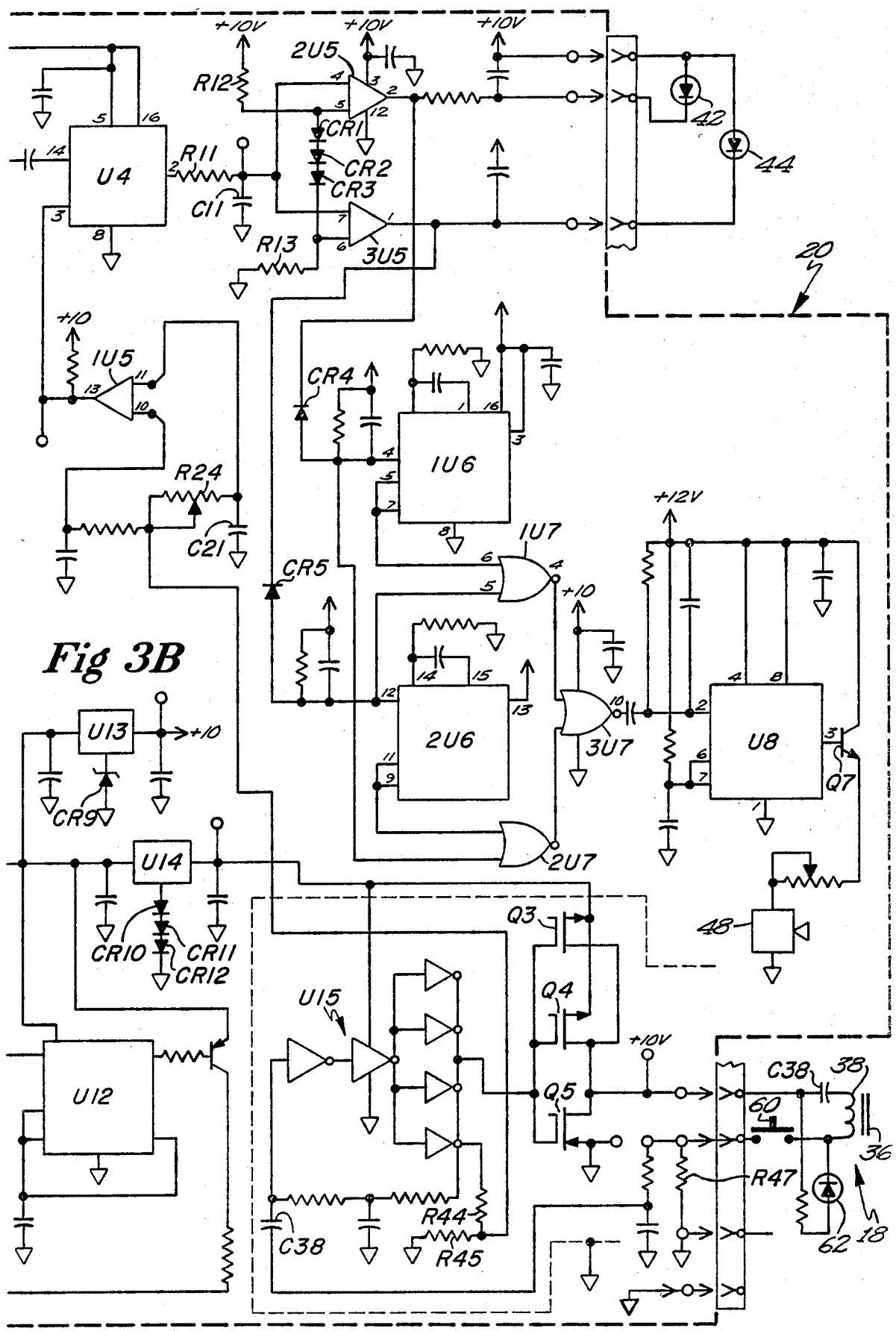

Having presented the foregoing information, it is believed that it will now be helpful to describe the electrical circuitry that has proved quite satisfactory in actual practice. Therefore, reference will be made to FIGS. 3A and 3B, which together constitute a circuit diagram exemplifying electronic controller 20. Attention is first directed to the upper left-hand corner of FIG. 3A where guidewire 22, core 24, coil 28 and leads 30, all components of detector 12, appear.

Controller 20 is composed of a number of sections. The first section to be referred to is the signal amplifier and selector section which is comprised of a transformer T1, a first operational amplifier U1, a second operational amplifier U2 and an analog switch U3. The signal received from detector 12 via guidewire 22 is coupled into the primary of transformer T1, which in practice is a 1:10 step-up transformer. The secondary of transformer T1 is connected to op amp U1 which amplifies the signal, providing a gain in the preferred form in the range of 200. The amplified signal from op amp U1 is delivered to op amp U2, this second op amp U2 having a gain in the preferred form in the range of 4. Analog switch U3 may be, for example, an Intersil quad switch DG201A.

Inasmuch as the circuit represents the actual circuitry that has been embodied in apparatus 10, it will be pointed out at this stage that the apparatus has two modes, one being a "normal" mode and the other a "deep" mode. It is the function of analog switch U3 to select the output from op amp U1 for a normal mode operation and the output from op amp U2 for the deep mode operation. Analog switch U3 also controls the energization of a "normal" indicator 72 and a "deep" indicator 74. It should be noted that the amplified signal from op amp U1, when controller 20 is operating in its normal mode, is delivered directly to a phase detector U4 (which will be referred to in greater detail hereinafter), whereas when operating in the "deep" mode, the signal from op amp U1 is additionally amplified through the agency of second op amp U2 and then delivered to phase detector U4. As a practical matter, the signal delivered to phase detector U4 must be amplified to a minimum level of 700 millivolts peak-to-peak.

The next section to be described will be termed the locator coil driver comprised basically of an inverter U15, such as an RCA hex inverter CD4049BE, three field effect transistors Q3, Q4 and Q5, coil 38 of locator 34, a 0.01 microfarad capacitor C38 plus associated circuitry that need not be referred to in detail. What these components constitute is an oscillator circuit whose frequency is determined by the series resonant frequency as influenced by the inductance of locator coil 38 and the capacitance of capacitor C38. At the series resonant frequency, maximum current flows through coil 38 and therefore a maximum voltage is sensed across a resistor R47. This voltage, it will be observed, is fed back to inverter U15 which is capable of amplifying the signal to a level sufficient to drive FET transistors Q3, Q4 and Q5 to a maximum voltage swing. The use of the alluded to feedback insures that the current through coil 38 is always a maximum regardless of short-term or long-term changes in coil 38, capacitor C38 or in any of the associated circuitry appearing in the lower right-hand corner of FIG. 3B.

It will be seen that a portion of the oscillator output voltage is fed from the juncture of two resistors R44 and R45 through a phase shift network which includes a variable resistor R24 and a capacitor C21, the portion of the oscillator output voltage then being fed to a comparator 1U5. Comparator 1U5 amplifies the oscillator signal level to provide a maximum voltage swing which voltage signal is applied to phase detector U4.

Describing in greater detail the role played by phase detector U4, it will be understood that phase detector U4 receives the amplified signal derived from detector 12 and the coil driver voltage supplied by comparator 1U5, detector U4 comparing the phase of these two voltage signals. Phase comparator U4 may be, for example, a CD4046BCN comparator manufactured by National Semiconductor. When locator 34 is in a proximal relation with coil 28 of detector 12 as diagramatically illustrated as position III in FIG. 1, then the two voltages are in phase with each other, producing a high average voltage output from phase detector U4 at its pin 2. This voltage is smoothed by a resistor R11 and a capacitor C11 to a DC level that in practice approximates +7 to +9 volts. This smoothed voltage is then impressed on pin 4 of a comparator 2U5, causing its output pin 2 to be driven toward zero volts and thus turning on amber indicator (LED) 42. However, when locator 34, more specifically its coil 38, is distal to coil 28 of detector 12 as diagramatically illustrated as position I in FIG. 1, the two voltages are out of phase by approximately 180°, thereby producing a low DC voltage at pin 4 of comparator 2U5 and also at pin 7 of another comparator 3U5, thus turning off amber indicator 42 and turning on red indicator 44, also an LED. Although not believed completely necessary to mention, it will be understood that two resistors R12, R13 and three diodes CR1, CR2 and CR3 form a network that establishes the turn-on threshold levels for the second input pins 5 and 6 of comparators 2U5 and 3U5. Thus, phase detector U4 and comparators 2U5 and 3U5 function to turn on either indicators 42 or 44.

Turning now to what constitutes an audible "beep" circuit for energizing beeper 48, it will be observed that the two output pins 2 and 1 of comparators 2U5 and 3U5 are connected to amber and red indicators 42 and 44, the output signals from comparators 2U5 and 3U5 being forwarded through diodes CR4 and CR5 to monostable multivibrators 1U6 and 2U6, such as an RCA dual monostable multivibrator CD4538BE. More specifically, when either amber or red indicator 42 or 44 has been on and then turned off, the corresponding monostable multivibrators 1U6 (pin 4) or 2U6 (pin 12), there being two such multivibrators incorporated into the designated RCA dual device CD4538BE, the corresponding monostable multivibrator is triggered, producing a 300-millisecond pulse at the corresponding output from the particular multivibrator 1U6 (pin 7) or 2U6 (pin 9).

The monostable output pulses and the input trigger pulses are delivered to NOR gates 1U7 and 2U7 in such a way that the following sequence of events occurs. Assume for the sake of discussion that amber indicator or LED 42 has been on, and that locator 34 is moved, then amber indicator or LED 42 turns off. Corresponding monostable multivibrator 1U6 or 2U6 is triggered via pin 4 as far as multivibrator 1U6 is concerned and triggered via pin 12 as far as multivibrator 2U6 is concerned, producing a 300-millisecond pulse at out-put pin 7 of multivibrator 1U6 or at output pin 9 of multivibrator 2U6. The monostable output pulses are applied to NOR gate 3U7. Monostable multivibrator 1U6 by way of its pin 7 produces a low level 300-millisecond pulse applied to pin 6 of NOR gate 1U7. However, if locator 34 is moved so that red indicator or LED 44 turns on within 300-milliseconds, a low voltage is produced at pin 1 of comparator 3U5, this voltage then being applied to pin 5 of NOR gate 1U7, doing so through diode CR5. Two low levels into NOR gate 1U7, that is via its pins 6 and 5, produce a high voltage level at output pin 4 of NOR gate 1U7. This high level causes a negative-going pulse at output pin 10 of NOR gate 3U7 to trigger a monostable multivibrator U8 which in turn produces a high-level pulse that causes beeper 48 to emit an audible sound. It is by means of an NPN transistor Q7 that the requisite amount of current is supplied to beeper 48.

It is important to note that if red indicator 44 turns on after 300 milliseconds, pin 6 of NOR gate 1U7 is, under these circumstances, at a high level and the low level on pin 5 thereof has no effect. Consequently, no trigger pulse is produced to drive monostable multivibrator U8, and beeper 48 remains silent. A similar sequence occurs when going from an on condition of red indicator 44 to an on condition of amber indicator 42.

Attention is now directed to what will be termed a power turn-on circuit comprised of monostable multivibrator U9 which functions as a "de-bouncer," multivibrator U9 being connected to a flip-flop or toggle circuit U10. Flip-flop U10 is wired so that when battery 66 is connected to controller 20, flip-flop U10 is reset through a capacitor C28. Pin 12 of flip-flop U10 goes high, thereby turning off a field effect transistor Q6. When this occurs, battery 66 is, in effect, disconnected from controller 20, at least the major portion thereof. However, components U9 and U10 are always energized when battery 66 is connected, but because these components are CMOS integrated circuit devices, their current draw is extremely low (less than 2 microamperes). When switch 76 is momentarily depressed, multivibrator U9 puts out a pulse which toggles flip-flop U10 so as to turn on transistor Q6, thereby connecting battery 66 to the rest of the circuit.

Inasmuch as a feature of the invention is to enable apparatus 10 to operate in either a normal mode or a deep mode, the normal/deep turn-on circuit portion of controller 20 will now be described. Basically, it includes monostable multivibrator U16, such as one-half of an RCA dual monostable multivibrator CD4538BE. Also the normal/deep turn-on circuitry includes a flip-flop U17 and a switch 68. When switch 68 is closed to cause controller 20 so supply power, controller 20 comes on in its normal mode. This causes the +10 volt DC bus to rise, forwarding a positive pulse through a capacitor C25 to pin 10 of flip-flop U17. Pin 10 is the "reset" pin of flip-flop U17. When reset pin 10 goes positive, the Q output on its pin 13 goes low, causing the previously mentioned analog switch U3 to be switched into its normal mode operation in that pin 6 belonging to amplifier U1 is then connected to pin 14 of phase detector U4 via pins 6 and 7 of switch U3. Monostable multivibrator U16 functions as a "de-bouncer." More specifically, when switch 68 is momentarily depressed by the operator, such action pulls pin 11 of multivibrator U16 low, thereby triggering a 200-millisecond pulse at output pin 10 of multivibrator U16 which then "toggles" flip-flop U17 into the desired deep mode operation. When output pin 12 of flip-flop U17 goes low, an electrical path is established between pins 2 and 3 of switch U3. This opens the circuit between pins 6 and 7 that was established for the normal mode operation so that the deep operational mode results. Indicator 72, when lighted by reason of an electrical path being established between pins 10 and 11 of switch U3, signifies a normal mode operation, whereas indicator 74, when lighted by reason of an electrical path being established between pins 14 and 15 of switch U3, signifies a deep mode operation.

Reference will now be made to two voltage regulators U13 and U14, such as those marketed by National Semiconductor as Model LM7805CT. All that really need be appreciated is that regulator U13 is a standard three-terminal +5 volt DC regulator. When its ground pin is connected to a 5-volt zener diode CR9, the resulting circuit forms a +10 VDC regulator. The +10 VDC powers the majority of the components contained in the circuitry constituting controller 20. The other regulator U14, together with diodes CR10, CR11 and CR12, forms a +7 VDC regulator which powers only the oscillator containing inverter U15 and transistors Q3, Q4 and Q5 (and coil 38) therein.

Should the voltage supplied by battery 66 become too low, actually below the required 11.5 VDC, such a condition should be made known to the user of apparatus 10. Therefore, a comparator U11, such as manufactured by Intersil, Model ICL7665S, having an internal constant voltage source is employed. The voltage from battery 66 is impressed on a voltage divider comprised of resistors R34, R35, R36 and R37, the battery voltage being compared to the internal voltage of comparator U11. More specifically, it will be noted that the junction between resistors R34 and R35 is connected to input pin 2 of comparator U11 and the junction of resistors R35 and R36 is connected to pin 3 of comparator U11. Thus, when the battery voltage is higher than +11.5 VDC, pin 1 of comparator U11 is low, thereby driving pin 7 of timer U12 low so as to turn on a transistor Q2 and thereby turn on the "on" indicator or LED 62. On the other hand, when the battery voltage goes below +11.5 VDC, pin 1 of comparator U11 goes high and timer U12 which is actually a free-running multivibrator, flashes "on" indicator 78 at approximately 2-to-3 pulses per second.

Reference will now be made to jack J4 which is used when battery 66 is to be charged. Thus, when the battery charger (not shown) is connected to controller 20, the charging current flows through a current limiting resistor R51 that is connected to jack J4 through a fuse F1. The current from resistor R51 flows through an isolating diode CR6 which prevents charge indicator 70 from draining battery 66. The voltage from the charger is impressed on pin 10 of flip-flop U10 via a diode CR7; pin 10 of flip-flop U10 is a reset pin. This keeps flip-flop U10 in a power off state, preventing the use of controller 20 while the charger is connected. Hence, apparatus 10 is rendered inoperable whenever battery 66 is connected to a charger via jack J4. In other words, the charger, which as already explained, must be disconnected from controller 20 in order for apparatus 10 to be used.

Reference has been made to the salient components that comprise source 18 and controller 20. In order to present a complete circuit, however, various associated components have been shown in the schematic drawing., even though it is not believed necessary to refer specifically to these associated components for an understanding of how apparatus 10 is to be employed, especially when the description of the circuitry is considered in conjunction with the earlier physical description of the various components exemplifying apparatus 10.

Now that the basic construction of apparatus 10 has been explained, the operation and advantages can be set forth and appreciated. Specifically, catheter 16 including detector 12 and guidewire 22 may be introduced into the venous or arterial system and advanced using standard catheter placement techniques. When a predetermined length of catheter 16 has been introduced, the handle of the locator 34 may be grasped by the clinician using a sterile technique and switch 60 should be actuated to provide AC current to source 18 of locator 34. Locator 34 may be positioned against the patient's skin and maneuvered along the vessel pathway into which catheter 16 was inserted. When locator 34 approaches tip 14 of catheter 16 as diagramatically illustrated as position III in FIG. 1, detector 12 will react to the magnetic field propagated by source 18 developing a small voltage which is in phase with the alternating current supplied by source 18 resulting in amber indicator 42 lighting up indicating that locator 34 is approaching the location of detector 12 and thus tip 14 of catheter 16. Continuing along the expected catheter path, when source 18 of locator 34 is located directly above detector 12 such that the flux lines of source 18 are perpendicular to the axis of detector 12 diagramatically illustrated as position II of FIG. 1, detector 12 does not develop a voltage resulting in amber indicator 42 going out. When source 18 of locator 34 passes beyond detector 12 as diagramatically illustrated as position I of FIG. 1, detector 12 will react to the magnetic field transmitted by source 18 developing a small voltage which is 180° out of phase from the alternating current generated for source 18 resulting in red indicator 44 lighting up and thus indicating that locator 34 has passed beyond tip 14 of catheter 16. Beeper 48 will emit a short audible "beep" when indicators 42 and 44 change from amber to red and red to amber. As diagramatically illustrated as position II in FIG. 1, indicators 42 and 44 may flash alternately due to motion of detector 12 in the vena cava with normal respiration and heartbeat.

By moving locator 34 including source 18 back and forth along the catheter pathway, the clinician is given a positive indication that the mid-axis of the transmitted electromagnetic energy field of source 18 is exactly over detector 12 located at tip 14 of catheter 16 by the alternate flashing of indicators 42 and 44 and the audible signal of beeper 48. The location of tip 14 in the vascular bed has then been established with respect to external anatomical landmarks. Adjustment of catheter 16 by further insertion into or retraction from the insertion site can then be made and the location of tip 14 of catheter 16 established utilizing apparatus 10 according to the teachings of the present invention set forth until the location of tip 14 has been established at the external anatomical landmark consistent with the desired endpoint location of tip 14 of catheter 16.

It can then be appreciated that if neither indicators 42 nor 44 light up, it is possible that catheter 16 may have followed an alternate pathway. In such instances, the location of detector 12 may be found by maneuvering locator 34 along potential alternate pathways of catheter 16 until the location of tip 14 of catheter 16 is determined. Repositioning of catheter 16 may be necessary if the alternate pathway utilized by catheter 16 is not satisfactory.

Similarly, if red indicator 44 is the first to light up, caution should be exercised as catheter 16 may have doubled back or followed an alternate pathway directed back toward the insertion site of catheter 16. If the amber indicator 42 does not light up, locator 34 may have been initially positioned beyond tip 14 of catheter 16. In any case, the location of detector 12 may be found by maneuvering locator 34 along the skin of the patient and adjustment and repositioning of tip 14 of catheter 16 may be necessary.

After determining that tip 14 of catheter 16 has been positioned in the correct position by use of apparatus 10 according to the teachings of the present invention, guidewire 22 including detector 12 attached thereto may be withdrawn from catheter 16 leaving catheter 16 in position within the venous or arterial system for use according to standard catheter techniques.

It can be appreciated that apparatus 10 according to the teachings of the present invention can be utilized along with and without interference from or with various surgical equipment where the magnetic field developed by source 18 does not affect and is not affected thereby including ECG and monitor, electrosurgical cautery, fluoroscopy, and electric patient table. Thus, apparatus 10 according to the teachings of the present invention provides realtime information during or following central venous catheterization regarding the positioning of tip 14 of catheter 16 for clinical alignment with an anatomical landmark. Further, the need for excessive irradiation exposure from fluoroscopy, X-ray, or the like to the patient and clinical staff may be eliminated from catheter placement procedures utilizing apparatus 10 according to the teachings of the present invention.

Further, it can be appreciated that apparatus 10 is easy to use to accurately determine the location of tip 14 of catheter 16 by clinical staff without requiring extensive training. Specifically, it is only necessary to move locator 34 until amber indicator 42 is lit indicating that locator 34 is approaching the location of tip 14 and that movement of locator 34 should be carefully continued until red indicator 44 is lit (and amber indicator 42 goes out) indicating that locator 34 has passed the location of tip 14 and forward movement of locator 34 should be stopped and reversed. Audible indication that locator 34 has passed over tip 14 is given by beeper 48. Thus, it is not necessary for the clinician to read or interpret meters or other complicated gauges which may result in potential misreading by the clinician. Rather, the present invention uses a traffic light type approach to indicate to the clinician the desired movement and positioning of locator 34. Further, as indicators 42 and 44 are provided in locator 34 with source 18, the clinician is able to receive visual indications at the external anatomical landmark of the patient and it is not necessary for the attention of the clinician to move away from the patient to read remote meters and/or gauges or to rely on other staff to provide such readings. Thus, full attention can be given by the clinician on moving locator 34 to determine the location of detector 12 of catheter 16 according to the teachings of the present invention.

Now that the basic teachings of the present invention have been explained, many extensions and variations will be obvious to one having ordinary skill in the art. For example, although detector 12 and source 18 in the most preferred form are associated with catheter 16 and locator 34, respectively, such association may be reversed in accordance with the teachings of the present invention.

Likewise, although utilization was explained having locator 34 maneuvered to locate tip 14 of catheter, it can be appreciated that locator 34 may be positioned at the external anatomical landmark consistent with the desired end-point location of tip 14 of catheter 16, and catheter 16 may be advanced using standard catheter placement techniques until positive indication is given by indicators 42 and 44 and beeper 48 of optimum placement of tip 14 of catheter 16.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. Apparatus for determining the location of a catheter inside biological tissue comprising, in combination: means for providing an external alternating current magnetic field; means for providing a first signal representative of the phase of the magnetic field; means contained in said catheter for developing a second signal when the catheter is in physical proximity to the magnetic field; means for comparing the phase of the second signal with that of the first signal; and means for indicating when a predetermined phase relationship exists between the first and second signals.

2. Apparatus for determining the location of a tip of a catheter inside biological tissue comprising, in combination: means for developing and transmitting an alternating current magnetic field; means for detecting the alternating current magnetic field and for developing an output voltage when in close physical proximity thereto; and means for comparing the alternating current of the magnetic field means and the output voltage of the detecting and developing means and for giving indication when the output voltage is in phase with the alternating current, when no output voltage is detected, and when the output voltage is 180° out of phase with the alternating current, with one of the magnetic field means and the detecting and developing means being removably positionable adjacent the tip of the catheter and the other of the magnetic field means and the detecting and developing means being positionable outside the biological tissue at landmarks consistent with the desired location of the tip of the catheter.

3. The catheter location determining apparatus of claim 2 wherein the comparing and giving means includes at least a first visual indicator positionable with the other of the magnetic field means and the detecting and developing means.

4. The catheter location determining apparatus of claim 3 wherein the comparing and giving means includes a second visual indicator positionable with the other of the magnetic field means and the detecting and developing means, with the first visual indicator providing a visual indication when the output voltage is in phase with the alternating current and the second visual indicator providing a visual indication when the output voltage is 180° out of phase with the alternating current.

5. The catheter location determining apparatus of claim 4 wherein the comparing and giving means includes means for producing an audible signal when indication changes from the first indicator to the second indicator and from the second indicator to the first indicator.

6. The catheter location determining apparatus of claim 2 wherein the magnetic field means comprises a core of magnetically permeable material and an encircling coil and wherein the detecting and developing means comprises a core of magnetically permeable material and an encircling coil, with the core of the other of the magnetic field means and the detecting and developing means being positionable generally perpendicular to the core removably positionable adjacent the tip of the catheter.

7. The catheter location determining apparatus of claim 6 wherein the detecting and developing means includes first and second amplifiers for amplifying any electrical signal detected by the coil, and switch means for by-passing one of said amplifiers to provide a different operational mode when said one amplifier is by-passed by said switch means.

8. The catheter location determining apparatus of claim 2 wherein the catheter includes a guidewire removably insertable in the catheter, with one of the magnetic field means and the detecting and developing means secured to the guidewire and positionable adjacent the tip of the catheter.

9. The catheter location determining apparatus of claim 2 wherein the magnetic field means is positionable outside the biological tissue and the detecting and developing means is removably positionable adjacent the tip of the catheter.

10. The catheter location determining apparatus of claim 2 including a battery; means for converting direct current supplied by said battery to alternating current for energizing the magnetic field means; and means for preventing the supply of direct current to said converting means when said battery is being charged so as to render the apparatus inoperable.

11. Method for determining the location of a tip of a catheter inside biological tissue comprising the steps of:

(a) providing means for developing and transmitting an alternating current magnetic field;
(b) means for detecting the alternating current magnetic field and for developing an output voltage when in close proximity to the magnetic field;
(c) removably positioning one of the magnetic field means and the detecting and developing means adjacent the tip of the catheter for entry into the biological tissue with the catheter;
(d) supplying alternating current to the magnetic field means;
(e) comparing the alternating current and the output voltage;
(f) moving the other of the magnetic field means and the detecting and developing means outside of the biological tissue at landmarks consistent with the desired locations of the tip of the catheter; and
(g) indicating when the output voltage is in phase with the alternating current, when no output voltage is detected, and when the output voltage is 180° out of phase with the alternating current.

12. The method of claim 11 wherein the indicating step comprises the steps of:
(a) providing a first visual indication when the output voltage is in phase with the alternating current;
(b) providing a second visual indication when the output voltage is 180° out of phase with the alternating current.

13. The method of claim 12 wherein the indicating step further comprises the step of:
(c) providing an audible signal when indication changes from the first visual indication to the second visual indication and from the second visual indication to the first visual indication.

14. The method of claim 11 wherein the removably positioning step comprises the steps of:
(a) providing a guidewire, with one of the magnetic field means and the detecting and developing means being secured to the guidewire; and
(b) positioning the guidewire within the catheter for entry into the biological tissue with the catheter.

15. The method of claim 11 wherein the removably positioning step comprises the step of removably positioning the detecting and developing means adjacent the tip of the catheter; and wherein the moving step comprises the step of moving the magnetic field means.

16. The method of claim 15 wherein the indicating step comprises the step of providing an indicator for providing a visual indication with the moving step further comprises the step of moving the indicator with the magnetic field means.

* * * * *

REEXAMINATION CERTIFICATE (1564th)
United States Patent [19]

Strohl, Jr. et al.

[11] B1 4,905,698
[45] Certificate Issued Oct. 1, 1991

[54] METHOD AND APPARATUS FOR CATHETER LOCATION DETERMINATION

[75] Inventors: Clair L. Strohl, Jr., Norfolk; Michael C. Ferragamo, N. Dighton; Donald A. Kay; Alan R. Shapiro, both of Sharon; Gary R. Whipple, S. Attleboro, all of Mass.

[73] Assignee: Pharmacia Deltec Inc., St. Paul, Minn.

Reexamination Request:
No. 90/002,090, Jul. 19, 1990

Reexamination Certificate for:
Patent No.: 4,905,698
Issued: Mar. 6, 1990
Appl. No.: 243,689
Filed: Sep. 13, 1988

[51] Int. Cl.⁵ .............................................. A61B 6/12
[52] U.S. Cl. .............................. 128/653 R; 128/737; 600/13; 324/219; 324/239
[58] Field of Search ........................... 128/653 R, 737

[56] References Cited
U.S. PATENT DOCUMENTS
4,173,228 11/1979 Van Steenwyk et al.
4,176,662 12/1979 Frazer.

*Primary Examiner*—Ruth S. Smith

[57] ABSTRACT

A method and apparatus (10) for determining accurately the location of the tip (14) of a catheter (16) inside biological tissue is disclosed including a locator (34) having a coil (38) wound axially on a core (36) and a detector (12) in the form of a coil (28) wound on a core (24) removably positionable within catheter (16) adjacent the tip (14). A controller (20) generates AC current to coil (38) to produce an electromagnetic field and compares it with the output voltage developed in coil (28) when the locator (34) comes within close physical proximity to detector (12). Locator (34) includes an amber LED indicator (42) which is energized when the locator (34) is behind the detector (12) and the monitored output voltage is in phase with the generated alternating current and includes a red LED indicator (44) which is energized when the locator (34) is beyond the detector (12) and the monitored output voltage is 180° out of phase with the generated alternating current. The controller (20) includes a beeper (48) which provides an audible indicator when energization changes between the indicators (42, 44).

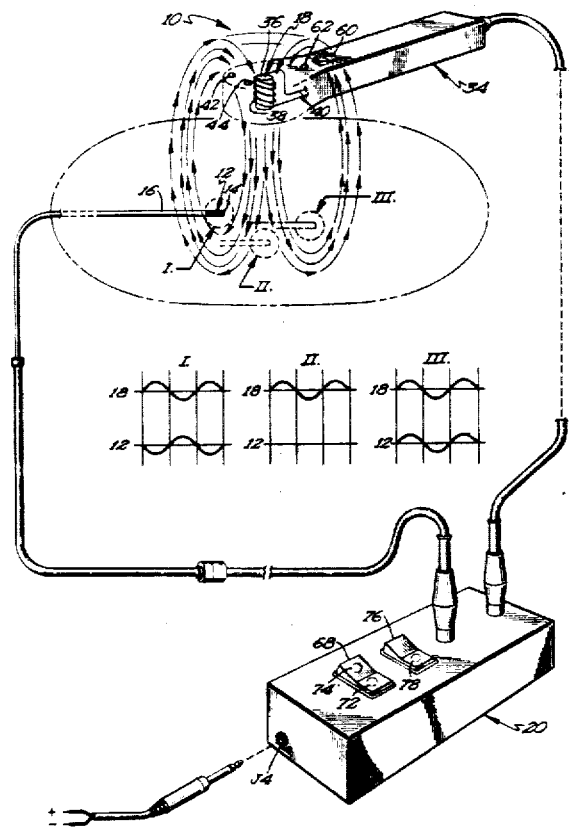

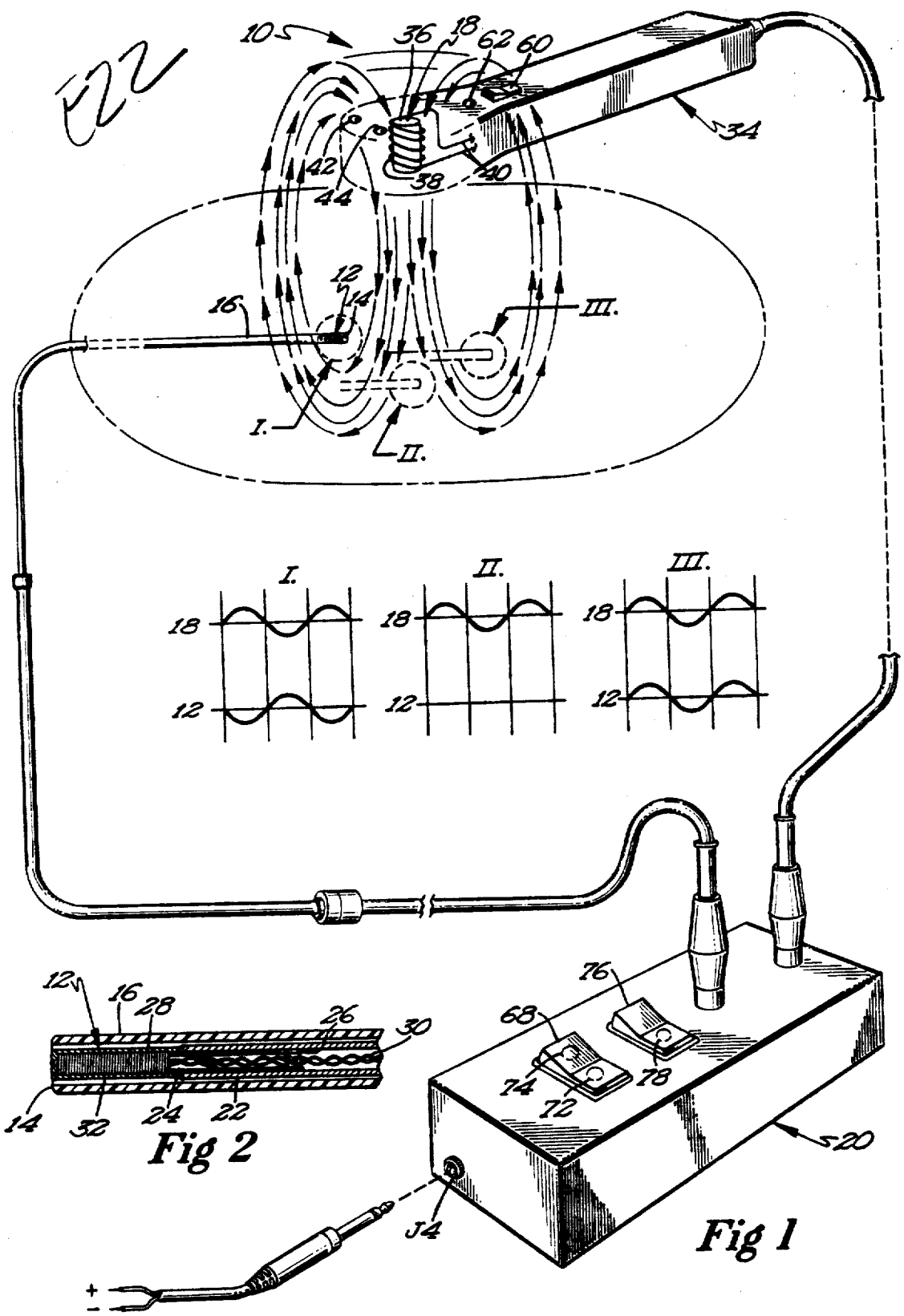

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, 9, 11, 15, and 16 are cancelled.

Claims 3–8, 10, and 12–14 are determined to be patentable as amended.

New claims 17–21 are added and determined to be patentable.

3. The catheter location determining apparatus of claim [2] *17* wherein the [comparing and giving] *electronic* means includes at least a first visual indicator positionable with the [other of the magnetic field means and the detecting and developing] *energy source* means.

4. The catheter location determining apparatus of claim [3] *18* wherein the [comparing and giving] *electronic* means includes a second visual indicator positionable with the [other of the magnetic field means and the detecting and developing] *energy source* means, with the first visual indicator providing a visual indication when the [output voltage] *phase transition* is in phase [with the alternating current] and the second visual indicator providing a visual indication when the [output voltage] *phase transition* is [180°] out of phase [with the alternating current].

5. The catheter location determining apparatus of claim [4] *18* wherein the [comparing and giving] *electronic* means includes means for producing an audible signal when [indication changes from the first indicator to the second indicator and from the second indicator to the first indicator] *the phase transition sequence occurs.*

6. The catheter location determining apparatus of claim [2] *17* wherein the [magnetic field] *energy source* means comprises a core of magnetically permeable material and encircling coil and wherein the detecting [and developing] means comprises a core of magnetically permeable material and an encircling coil, with the core of the [other of the magnetic field] *energy source* means [and the detecting and developing means] being positionable generally perpendicular to the core *of the detecting means* removably positionable adjacent the tip of the catheter.

7. The catheter location determining apparatus of claim 6 wherein the [detecting and developing] *electronic* means includes first and second amplifiers for amplifying any electrical signal detected by the coil, and switch means for by-passing one of said amplifiers to provide a different operational mode when said one amplifier is by-passed by said switch means.

8. The catheter location determining apparatus of claim [2 wherein the catheter includes] *17 further including* a guidewire removably insertable in the catheter [with one of the magnetic field means and the detecting and developing means] *lumen, with the detecting means* secured to the guidewire and positionable adjacent the tip of the catheter.

10. The catheter location determining apparatus of claim [2] *17* including a battery; means for converting direct current supplied by said battery to alternating current for energizing the [magnetic field] *energy source* means; and means for preventing the supply of direct current to said converting means when said battery is being charged so as to render the apparatus inoperable.

12. The method of claim [11] *21* wherein the [indicating] *determining* step [comprises the steps of:] *includes* [(a)] providing a first visual indication when the *alternating* output voltage is in phase with the alternating current; [(b)] *and* providing a second visual indication when the *alternating* output voltage is [180°] out of phase with the alternating current.

13. The method of claim 12 wherein the [indicating] *determining* step further [comprises the step of: (c)] *includes* providing an audible signal [when indication changes from the first visual indication to the second visual indication and from the second visual indication to the first visual indication] *upon the occurrence of the phase transition sequence.*

14. The method of claim [11] *19* wherein the [removably positioning step comprises the steps of:] *providing step includes:*
 (a) providing a guidewire, with [one of the magnetic field means and the detecting and developing means] *the detecting means* being secured to the guidewire; and
 (b) positioning the guidewire within the catheter for entry into the biological tissue with the catheter.

*17. An apparatus for use with a catheter, said catheter having a tip and a lumen, and the apparatus being suitable for determining the location of the tip of the catheter inside biological tissue, comprising:*
 *energy source means for generation of an alternating current magnetic field, which means is adapted to be positionable outside the biological tissue according to external anatomical landmarks consistent with the approximate location of the tip of the catheter and is adapted to cause the flux lines of the field to be essentially perpendicular to the plane of the tissue surface;*
 *detecting means for development of an alternating output voltage in reaction to the alternating current magnetic field when in close proximity to the energy source means, the detecting means being adapted to be removably positioned within the catheter lumen at the catheter tip;*
 *electronic means for connection with the energy source means and the detecting means, the electronic means being adapted for determination of the region of the alternating current magnetic field which develops zero net alternating output voltage in the detecting means when the energy source means is moved in close proximity and in a relative perpendicular arrangement past the detecting means, said determination providing a single coordinate of the location of the catheter tip.*

*18. An apparatus according to claim 17 wherein the electronic means is adapted for determination of a phase transition sequence of in-phase and out-of-phase as well as an opposite phase transition sequence between the alternating current of the energy source means and the alternating* output voltage when the energy source means is moved in close proximity and in a relative perpendicular arrangement past the detecting means.

19. A method for use with a catheter having a tip and a lumen, the method determining the location of the tip of the catheter inside biological tissue, comprising:

providing within the tip portion of the catheter lumen a detecting means for development of an alternating output voltage in reaction to an alternating current magnetic field in close proximity to the detecting means;

passing an energy source means over the outside of the biological tissue according to anatomical landmarks consistent with the approximate location of the catheter tip, the energy source means generating the alternating current magnetic field with flux lines essentially perpendicular to the plane of the tissue surface and developing the alternating output voltage in the detecting means when the energy source means and the detecting means are in close proximity and in perpendicular relation;

determining a single coordinate of the location of the catheter tip by meansuring a planar region within which the alternating current magnetic field develops zero net output voltage in the detecting means as the energy source means is moved in close proximity and in perpendicular relation past the detecting means.

20. A method according to claim 19 which further comprises determining the location of the catheter tip by combining the single coordinate of the determining step with the anatomical landmarks indicating the biological tissue in which the catheter is located.

21. A method according to claim 19 wherein the measuring is accomplished by finding a phase transition sequence of in-phase and out-of-phase, or an opposite phase transition sequence, between the alternating current and the alternating output voltage as the energy source means is moved in close proximity and in a relative perpendicular arrangement past the detecting means.

* * * * *